(12) United States Patent
McConville et al.

(10) Patent No.: US 11,369,631 B1
(45) Date of Patent: *Jun. 28, 2022

(54) ORAL GELLING LIQUID FORMULATIONS

(71) Applicants: Jason Thomas McConville, Albuquerque, NM (US); Elnaz Sadeghi, Goleta, CA (US)

(72) Inventors: Jason Thomas McConville, Albuquerque, NM (US); Elnaz Sadeghi, Goleta, CA (US)

(73) Assignee: UMM Rainforest Innovations, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,385

(22) Filed: Apr. 3, 2020

Related U.S. Application Data

(60) Provisional application No. 62/828,900, filed on Apr. 3, 2019.

(51) Int. Cl.
*A61K 33/16* (2006.01)
*A61K 47/38* (2006.01)
*A61K 9/06* (2006.01)

(52) U.S. Cl.
CPC ............... *A61K 33/16* (2013.01); *A61K 9/06* (2013.01); *A61K 47/38* (2013.01)

(58) Field of Classification Search
CPC .......... A61K 33/16; A61K 47/38; A61K 9/06
See application file for complete search history.

(56) References Cited

U.S. PATENT DOCUMENTS

2015/0374633 A1* 12/2015 Fedorchak ............. A61K 47/34
424/501

OTHER PUBLICATIONS

Sadeghi (2018), Publication Dec. 17, 2018.*

* cited by examiner

*Primary Examiner* — Shirley V Gembeh
(74) *Attorney, Agent, or Firm* — Gonzales Patent Services; Ellen M. Gonzales

(57) ABSTRACT

A gelling liquid formulation comprising a thermoresponsive hydrogel modified with an agent that reduces the alters the native gelation point of the thermoresponsive hydrogel and methods for making and using the same.

12 Claims, 6 Drawing Sheets

ORAL GELLING LIQUID FORMULATIONS

CROSS-REFERENCE TO RELATED APPLICATIONS

The following application claims benefit of U.S. Provisional Application No. 62/828,900, filed Apr. 3, 2019, which is hereby incorporated by reference in its entirety.

SUMMARY

According to various embodiments the present disclosure provides gelling liquid formulations comprising a thermoresponsive hydrogel modified with an agent that reduces the alters the native gelation point of the thermoresponsive hydrogel and methods for making and using the same.

BRIEF DESCRIPTION OF THE DRAWINGS

FIG. 4A depicts formation of cage like structure.

FIG. 4B shows disruption of water cages by sodium fluoride.

FIG. 4C shows hydrophobic association.

FIG. 4D shows formation of the hydrogel.

DETAILED DESCRIPTION

Figure 1:
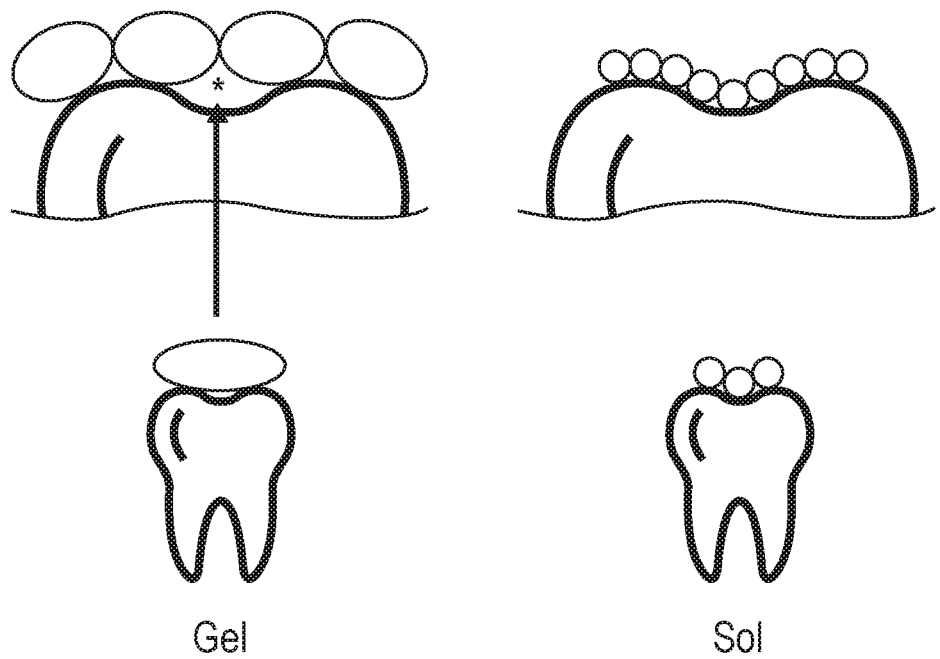
FIG. 1 is a schematic illustration of fluoride application in the form of sol or gel. The gel form of fluoride is not effectively applied into deep areas of the tooth while it is more efficiently applied as a sol.

According to various embodiment the present disclosure provides formulations for an oral gelling liquid and methods and uses therefore. According to a specific embodiment, the present disclosure provides methods for altering the thermal gelation temperature of thermoresponsive hydrogels such as, for example, hypromellose. Specifically, the present disclosure provides methods for altering the gelation temperature of a thermoresponsive hydrogel from its "natural" gelation temperature to an "altered" gelation temperature. According to a further embodiment, the present disclosure provides method for altering the thermal gelation temperature of a thermoresponsive hydrogel from a temperature that is not at, around, or below body temperature to a temperature that is at, around, or below body temperature. Furthermore, where temperature is the only factor that initiates gelation, and no other chemical or environmental stimuli are required, these types of formulations could be a safe approach for in situ gelation at body temperature [23]. In situ gelation of a pharmaceutical formulation may also enable sustained release of a given drug at the site of administration, and so could be a means to enhance therapeutic effectiveness. Accordingly, as specific examples, thermoresponsive hydrogels with a gelation temperature at, around, or below body temperature may be useful, for example, in drug/therapeutic agent delivery, dental treatment, or other applications.

Thermoresponsive hydrogels are polymers that show a phase transition(s) (e.g. sol-gel transition) at specific temperatures. For the purposes of the present disclosure, a thermoresponsive hydrogel's "native" gelation point is considered to be, for example in the case of hypromellose that of a 2% w/v solution for a given polymer grade and molecular weight. Thermoresponsive hydrogels are of particular interest for biomedical and pharmaceutical applications, including, but not limited to, gene delivery, drug delivery, and tissue engineering [18]. The appeal of these hydrogel systems is that they can be used in a liquid state or solution (sol) at a first temperature (i.e. ambient or "room" temperature) before transitioning into a viscoelastic solid (gel) at another temperature (i.e. "body temperature"). For the purposes of the present disclosure, the term "body temperature" in reference to a human subject is intended to mean approximately 37° C. It will be understood, of course, that average body temperatures can vary between various species and even between individual subjects and thus the appropriate gelation temperature for a particular purpose may be determined by the specific subject and conditions. Likewise, ambient conditions may vary depending on the intended purpose, similarly affecting the desired default temperature for the liquid or sol state of the thermoresponsive hydrogel. However, for the purpose of clarity, but without intending to be limited, for the purposes of the present disclosure, ambient temperatures are generally considered to be between 15 and 25° C.

According to a first embodiment, the present disclosure provides a method for modifying a suitable thermoresponsive hydrogel with a thermal gelation temperature ($T_{gel}$) modifying agent, which may take the form of a "gelling aid". For the purposes of the present disclosure, the term "gelling aid" is intended to mean an additive to assist in gelation of a polymeric ingredient.

Suitable thermoresponsive hydrogels may include but are not limited to: copolymeric hydrogel mixtures (e.g. poly(DL-lactide-co-glycolide) and poly(DL-lactide-co-E-caprolactone)), gelling mixtures (e.g. N-[(2-hydroxy-3-methyltrimethylammonium)propyl], chitosan chloride, and poly (ethylene glycol)), glycosaminoglycans (e.g. chrondroitins, heparin, hyaluronic acid, keratin), micellar gelling systems (e.g. poly(N-isopropylacrylamide)-block-poly(sulfobetaine methacrylate) (PNIPAAm-b-PSBMA) block, organogels (e.g. 4-tertbutyl-1-aryl cyclohecanol derivatives, Boc-Ala (1)-Aib(2)-ß-Ala(3)-OMe, fatty acids and n-alkanes, N-lauroyl-L-lysine ethylester, poly(ethylene glycol), polycarbonates, polyesters and poly(alkylene)), phycocolloids (e.g. agars, alginates, carageenans), polyacrylic type gels (e.g., poly-(N-isopropyl acrylamide), polyacrylic and polymethacrylic acid and derivatives), polyesters (e.g. PLA, PLGA), polysaccharide type gels (e.g. cellulose and derivatives, chitosan and derivatives, gellan gum, glucomannan, modified dextrans, starch and derivatives, xanthan gum, xyloglucans), protein type gels (e.g. albumen, collagen, fibrin, pectin, silk fibroin), thermoresponsive terpolymers complexes (e.g. N-isopropylacrylamide, hydroxyethyl methacrylate, and 2-acrylamido-2-methylpropane sulfonic acid), thermoresponsive vitrimers and composites (e.g. polyurethane-forming components with functional groups), triblock polymer systems (e.g. poly(DL-lactide)-block-poly(ethylene glycol)-block-poly(DL-lactide), poloxamers).

Suitable gelling aids may include, but are not limited to compounds that contain "salt-out-anions" such as 2-(2-methoxyethoxy)ethylsulfate, 2-carboxybenzoate, Acetate, Aluminumtetrachlorate, Aspartate, Benzoate, bis(trifluoromethyl)azanide, bis(trifluoromethylsulfonyl)imide, bis(trifluoromethylsulfonyl)methane, Bromide, Carbonate, Chloride, Choline, Citrate, Decanoate, Dibutylphosphate, Dicyanamide, Diethylphosphate, Dimethylphosphate, Dodecylbenzenesulfonate, Ethoxyethylsulfate, Ethylsulfate, Fluoride, Fumerate, Guanidinium, Hexafluorophosphate, Hydrogen carbonate, Hydrogen phosphate, Hydrogensulfate, Iodide, Imadozolium, Lactate, Malate, Maleate, Methanoate, Methanesulfonate, Methoxyethylsulfate, Methylphosphate, Methylsulfate, Morpholinium, Nitrate, Nitrite, Octylsulfate, Oxalate, Perchlorate, Phosphate, Phosphonium, Picrate, Piperidinium, Propionate, Pyridinium, Pyrolidinium, Salicylate, Succinate, Sulfate, Sulfonate, Tetracyanoborate, Tetrafluoroborate, Tetrafluorophosphate, Thiocyanate, Trichloroacetate, Toluene-4-sulfonate, Tricyanomethanide, or Tri-fluoro-methane, Tri-fluoro-methanesulfonate and the like). Additionally gelling aids may include, but are not limited to compounds that contain to "salt-out-cations" such as Aluminum, Ammonium, Aminopyridines, Barium, Beryllium, Calcium, Cobalt, Copper, Iron, Lithium, Magnesium, Manganese, Nickel, Potassium, Sodium, Tetraethyl Ammonium, Tetramethyl Ammonium, Zinc salts and the like. For the purposes of the present disclosure, the terms "salt-out anion" and "salt-out cation" are intended to mean either an anion or cation that has a strong affinity for water and hydration, respectively. Other gelling aids may include agents having a high affinity for water that can further promote gelation of polymers. Moreover, a combination of gelling aids may be used.

According to various embodiments, the oral gelling liquid is a cellulose derivative modified with a gelling agent. Examples of cellulose derivatives include, for example, methyl cellulose, and hydroxypropyl methylcellulose, and the like.

Cellulose derivatives have gained popularity among the available thermoresponsive polymers for their potential usefulness in biomedical and pharmaceutical fields. These polymers are biodegradable, have low toxicity, and are obtained from renewable sources [15].

Cellulose is the most abundant natural polymer, having a repeating structure of anhydroglucose units [45]. Cellulose itself is insoluble in water because of strong intramolecular hydrogen bonding between cellulose polymer chains. It is insoluble in water, this complicates its use in bioprocesses.

Etherification of a specific fraction of hydroxyl groups within the cellulose polymer structure yields water-soluble cellulose derivatives. Substituents decrease intramolecular hydrogen bonding and force the polymer chains to closely interact [11]. However, etherification of all hydroxyl groups with hydrophobic groups results in the synthesis of insoluble cellulose derivatives [30]. The "extent" or "degree of substitution" refers to the average number of substituted hydroxyl groups per anhydroglucose unit. The optimum degree of substitution is between 1.4 and 2, rendering the cellulose derivatives obtained water-soluble.

Three distinct types of bonding occur once a cellulose derivative is dissolved in cold water: (1) intramolecular hydrogen bonding between unaltered hydroxyl groups of polymer chains, (2) hydrogen bonding between water molecules and hydrogen groups of the hydrophobic polymer substituents, and (3) hydrophobic-hydrophobic interactions between the hydrophobic substituent groups. Hydrogen bonding decreases and the hydrophobic associations become more prominent at higher temperatures, leading to a reduction in the water solvent capacity; this results in thermal gelation [30]. The specific temperature where a viscoelastic solid structure is formed is known as the sol-gel transition temperature ($T_{Gel}$) [23].

Cellulose esters and cellulose ethers are two groups of cellulose derivatives with different substituents of the available hydroxyl groups present on the native cellulose. A common use for cellulose ethers is as rate controlling excipients for drug release, and as such they have been widely used as coating and film forming ingredients in pharmaceutical products [27].

In general, cellulose derivatives are biocompatible polymers which are of particular interest in the cosmetic, food, and pharmaceutical industries due to their broad applications that include acting as: binding agents, suspension aids, stabilizers, thickeners, film formers, and surfactants [16, 40, 8].

According to a specific embodiment, the oral gelling liquid is Hypromellose, or hydroxypropyl methylcellulose (HPMC) modified with a sodium fluoride (NaF) additive. Hypromellose or hydroxypropyl methylcellulose (HPMC), is a high purity excipient monographed in the USP [28]. The general formula for hypromellose is $C_8H_{15}O_8$—$(C_{10}H_{18}O_6)_n$—$C_8H_{15}O_8$.

Hypromellose, or hydroxypropyl methylcellulose (HPMC) has been widely used for biomedical and pharmaceutical applications due to its advantages, including that it is modifiable in terms of viscosity, and it has the ability to form thermally reversible hydrogels. The thermal gelation temperature ($T_{Gel}$) of a given HPMC solution strongly depends on its characteristic grade and the solution concentration. Applying certain additives can modify the $T_{Gel}$ even further; depending on their nature and concentration. With the addition of said additives, a lower or higher $T_{Gel}$ can be obtained. For example, the addition of sodium chloride (NaCl) reduces the $T_{Gel}$, whilst sodium iodide (NaI) increases the $T_{Gel}$, for a given HPMC solution. Therefore, for a certain application, the gelation temperature of a solution could be modified by adding a selected additive at an appropriate concentration.

Methyl and hydroxypropyl groups are attached to the cellulose structure via etherification. The resultant fraction of methoxy, hydroxypropoxy groups, as well as the molecular weight are the factors that can affect the physiochemical properties of hypromellose [36], [46], [3]. As mentioned above, the degree of substitution is the average number of methoxy groups per anhydroglucose subunit. The term molar substitution (MS) refers to the average number of hydroxypropoxy groups per anhydroglucose subunit. The methoxy groups in hypromellose are relatively hydrophobic domains, while hydroxypropoxy groups are relatively hydrophilic by contrast [10].

Four different types of hypromellose are listed in The U.S. Pharmacopeia (USP): hypromellose 2208, hypromellose 1828, hypromellose 2910, and hypromellose 2906 (United States Pharmacopeia Convention, 1980). With this numerical designation, the first two digits represent the nominal percentage of methoxy groups and the last two numbers are designated to the nominal percentage of the hydroxypropoxy groups. Table 1 identifies the maximum and minimum amount of methoxy and hydroxypropoxy for the four monographed hypromellose types, with the average values used in the naming system classification.

TABLE 1

Maximum/Minimum Methoxy/Hydroxyporpoxy

| Substitution | Methoxy (%) | | Hydroxypropoxy (%) | |
|---|---|---|---|---|
| Type | Mib. | Max. | Min. | Max. |
| 1828 | 16.5 | 20.0 | 23.0 | 32.0 |
| 2208 | 19.0 | 24.0 | 4.0 | 12.0 |
| 2906 | 27.0 | 30.0 | 4.0 | 7.5 |
| 2910 | 28.0 | 30.0 | 7.0 | 12.0 |

Hypromellose solutions are stable over a wide range of pH values, provide stable viscosity during long term storage conditions, and are widely used in pharmaceutical formulations [37]. The properties of a given solution of hypromellose are affected by the difference in degree of substitution, molar substitution, the concentration of hypromellose, and the amount and nature of additives, as well as the temperature.

Aqueous solutions of hypromellose are able to transform into viscoelastic solid gels upon heating. This phenomenon is reversible and plays a critical role in biomedical applications, such as drug release systems. It has been reported that the methoxy groups of hypromellose are important in the gelation process. [48]

It is believed, in aqueous solutions at low temperatures (below the thermal gelation temperature), that water molecules surround the hydrophobic methoxy groups, acting to form a cage-like structure. These structures are likely to exist due to water-water hydrogen bonding [25]. Therefore, at low temperatures the hypromellose is soluble in the water, however with an increasing temperature, and with an overall reduction in hydrogen bonding, a breakdown of the methoxy group water cages occurs; this in turn causes hydrophobic group exposure. Consequently, a hydrophobic association occurs, and this results in the formation of a 3D network and finally, a hydrogel structure is formed [24].

In general, the specific temperature or gelation rate at which this gelation occurs is dependent on the grade or substitution type of the selected polymer, its concentration, and the properties and concentration of other components. For example each grade of hypromellose demonstrates a different thermal gelation temperature due to differences in the substituent groups on the anhydroglucose subunits. For all different grades of hypromellose substitution, gelation temperature decreases with an increase in the concentration of the hypromellose solute [43].

Salts or ions are able to shift the $T_{Gel}$ of hypromellose solutions to lower or higher temperatures, based on their ability to decrease or increase the hydrophobicity of the hypromellose in water relative to a salt-free hypromellose solution [49]. "Salt-out" anions elevate solute hydrophobicity in water, whereas "salt-in" anions reduce solute hydrophobicity [21].

As mentioned above, water molecules form hydrogen bonds along the polymer chains and around the methoxy substituted groups. Increasing the temperature results in disruption of the water cages surrounding the methoxy groups, their aggregation, and the subsequent formation of gel. However, adding salts can change the $T_{Gel}$. Salt-out ions have a strong ability of hydration, so have more tendency to attract water molecules as compared to the polymer chains themselves. Therefore, once added into the solution, water molecules rapidly surround the salt, this directly causing the water-cages around the methoxy groups to be disrupted at lower temperatures. As a result, more hydrophobic groups are exposed and interact with each other at that lowered temperature, compared to comparable hypromellose solutions that do not contain any salt-out ions. Thus, the gelation effect occurs at lower temperature in the presence of these types of salts [49].

In contrast to salt-out ions, the mechanism of the salt effects on sol-gel transition for salt-in ions, such as the iodide ion (I⁻), is different. The iodide ion is a large negative ion which effectively is believed to cause water to intersperse throughout the polymer chains; this has a preventative effect on hydrophobic association and gelation. This preventative effect causes the gel to form at higher temperatures than a comparable salt-free hypromellose solution. Overall, it is believed that this phenomenon is related to weak interactions between these types of salts and water, and their lack of ability to break water-cage structures that surround the methoxy groups [48].

In situ gelation at body temperature is a type of delivery system that requires a "sol" phase at ambient temperature which turns into gel at body temperature. According to a specific embodiment, this the sol phase of the gel could be mixed with a drug or agent which is desired to be gradually delivered to specific location in a body. The sol phase (including the drug/agent) could then be injected into a body (for example into a wound or fissure) and the gel subsequently allowed to form in the body (at ~37° C.), entrapping the drug/agent during the gelation process. The entrapped drug/agent would then be gradually released from the hydrogel network. Accordingly, it is desirable to decrease the gelation temperature of a specific hypromellose solution from what is typically about 60° C. or greater to below that approximately 37° C.

Accordingly, in some embodiments, the gelling liquid has a low enough viscosity to be applied uniformly over the target surface. For example, the gelling liquid may have a viscosity that enables the liquid to be loaded into and then applied using a syringe, spray mechanism, or other similar apparatus.

The first step of drug release from a hypromellose containing formulation occurs during contact with an aqueous medium. Highly soluble small molecule drugs are released by a process of diffusion, through the gel layer and into a bulk aqueous media. For a hypromellose containing matrix tablet the mechanism is different for insoluble drugs, in this case the gel itself must dissolve and disperse at the aqueous interface (polymer erosion), and the insoluble drug is released during this process. A combination of these mechanisms can occur for a variety of different small molecule drugs, with varying physicochemical properties in tablet formulations. It remains unclear what the overall processes may be for an already formed hydrogel matrix. Studies have shown that drug release from swellable hydrophilic matrices is dependent on the thickness of the gel layer. Increasing in thickness of the gel results in slowing the rate of drug release [34]. In the presently described examples, the NaF active ingredient (as well as the salting out gelling aid) is water highly soluble, and thus the principle release mechanism was predicted principally to occur by diffusion.

As a specific embodiment, the presently described NaF modified hypromellose could be useful for a variety of dental treatments. For example, a mixture of HPMC and NaF in the form of a low viscosity solution (sol) may have applications for dental remineralization for deep areas of dental caries (prior to the onset of a cavity, that may only be treated by filling with a composite or amalgam). It is hypothesized that a subsequent gel, formed at body temperature, would be able to adhere to the cavities and gradually release the fluoride at the site where it is most needed; useful for preventing dental caries and repairing/reversing the initial tooth decay. Fluoride has been used for remineralization of teeth in dentistry. In addition it has been shown to reduce dental demineralization [1]. Demineralization is the process in which the important element calcium in teeth is depleted by the lactic acid, produced by bacteria in the oral cavity. Remineralization is the process in which the part of the tooth which has been demineralized can be replenished with calcium. The use of fluoride at the dental enamel automatically results in remineralization, since the fluoride is able to bind to calcium ions in the hydroxyapatite of enamel, whilst preventing bacteria from producing destructive lactic acid [1].

NaF comprises fluoride anions which are effective for the prevention of tooth decay. As such, a potential advantage of using NaF as a gelling aid with HPMC is the ability to administer fluoride as an in-situ gelation formulation, at body temperature. Currently, fluoride is delivered to teeth by different compositions such as: mouthwash, toothpaste, preformed gel, varnish, and foam. The main issue with the existing fluoride applications is an extremely low effective contact time of fluoride with teeth. On the other hand, using pre-formed gels for fluoride therapy is not altogether efficient because deep fissures and pits of dental caries do not efficiently receive enough direct fluoride contact due to the relative high viscosity of a pre-formed gel. FIG. 1 shows a schematic of the difference between fluoride application in the form of solution (sol) and a pre-formed gel in terms of receiving insufficient fluoride into deep area of dental caries. With this in mind, there is likely to be therapeutic advantage with the administration of fluoride in the solution state at the initial application into deep areas of tooth, where decay may occur. Following this application, a sol-gel transition at body temperature would be expected to allow for improved adherence and residence time at dental surfaces, whilst simultaneously prolonging the release time of fluoride. Accordingly, the present disclosure provides for the exploitation of the sol-gel transformation with a mixture of HPMC/NaF could be used functionally for in situ delivery of fluoride into deep areas of dental cavities.

Of course it will be understood that the approach of using a sol-gel transformation for dental purposes may also be useful for the delivery of other active pharmaceutical ingredients (APIs), such as antibiotics for the treatment of periodontal disease. Since the periodontal disease is caused by bacteria, both systemic and topical antibiotics are used to treat periodontal disease [33]. Therefore the sol-gel transformation could be used for topical antimicrobial therapy for periodontal disease.

Similarly, it should be realized that the presently described approach is not limited to remineralization or the use of topical antibiotics, but could also be used to deliver other APIs (e.g. antivirals, antifungals, corticosteroids, non-narcotic analgesics, narcotic analgesics, nonsteroidal anti-inflammatory drugs, local anesthetics, etc.).

While the disclosure herein is primarily focused on the thermal gelation properties of hypromellose, a widely used cellulose derivative in the pharmaceutical field, it will be understood that other cellulose derivatives or other polymers that demonstrate thermal gelation properties could also be used. Moreover, combinations of polymer grades or substitution types could be used to further optimize or fine tune gelation temperature.

Furthermore, while the disclosure herein is primarily focused on a reduction in thermal gelation properties of a given polymer using gelling aids such as salt-out anions, it will be understood that any additive/ingredient that acts to modify the thermal gelation properties of a polymeric system as described above could be used aids other cellulose derivatives or other polymers that demonstrate thermal gelation properties could also be used.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

[1] Abou Neel, E. A., Aljabo, A., Strange, A., Ibrahim, S., Coathup, M., Young, A. M., Bozec, L. and Mudera, V. 2016. Demineralization-remineralization dynamics in teeth and bone. *International Journal of Nanomedicine.* 11, (September 2016), 4743-4763. DOI:https://doi.org/10.2147/IJN.S107624.

[2] Acevedo, A., Takhistov, P., de la Rosa, C. P. and Florian, V. 2014. Thermal gelation of aqueous hydroxypropylmethylcellulose solutions with SDS and hydrophobic drug particles. *Carbohydrate Polymers.* 102, (February 2014), 74-79. DOI:https://doi.org/10.1016/j.carbpol.2013.11.017.

[3] Akinosho, H., Hawkins, S. and Wicker, L. 2013. Hydroxypropyl methylcellulose substituent analysis and rheological properties. *Carbohydrate Polymers.* 98, 1 (October 2013), 276-281. DOI:https://doi.org/10.1016/j.carbpol.2013.05.081.

[4] Almeida, N., Rakesh, L. and Zhao, J. 2014. Phase behavior of concentrated hydroxypropyl methylcellulose solution in the presence of mono and divalent salt. *Carbohydrate Polymers.* 99, (January 2014), 630-637. DOI: https://doi.org/10.1016/j.carbpol.2013.08.081.

[5] Arvidson, S. A., Lott, J. R., McAllister, J. W., Zhang, J., Bates, F. S., Lodge, T. P., Sammler, R. L., Li, Y. and Brackhagen, M. 2013. Interplay of Phase Separation and Thermoreversible Gelation in Aqueous Methylcellulose Solutions. *Macromolecules.* 46, 1 (January 2013), 300-309. DOI:https://doi.org/10.1021/ma3019359.

[6] Bain, M. K., Bhowmick, B., Maity, D., Mondal, D., Mollick, M. M. R., Rana, D. and Chattopadhyay, D. 2012. Synergistic effect of salt mixture on the gelation temperature and morphology of methylcellulose hydrogel. *International Journal of Biological Macromolecules.* 51, 5 (December 2012), 831-836. DOI:https://doi.org/10.1016/j.ijbiomac.2012.07.028.

[7] Bala, R., Pawar, P., Khanna, S. and Arora, S. 2013. Orally dissolving strips: A new approach to oral drug delivery system. *International Journal of Pharmaceutical Investigation.* 3, 2 (2013), 67-76. DOI:https://doi.org/10.4103/2230-973X.114897.

[8] Bodvik, R., Dedinaite, A., Karlson, L., Bergstrom, M., Bäverbäck, P., Pedersen, J. S., Edwards, K., Karlsson, G., Varga, I. and Claesson, P. M. 2010. Aggregation and network formation of aqueous methylcellulose and hydroxypropylmethylcellulose solutions. *Colloids and Surfaces A: Physicochemical and Engineering Aspects.* 354, 1 (February 2010), 162-171. DOI:https://doi.org/10.1016/j.colsurfa.2009.09.040.

[9] Byeon, S. M., Lee, M. H. and Bae, T. S. 2016. The effect of different fluoride application methods on the remineralization of initial carious lesions. *Restorative Dentistry & Endodontics.* 41, 2 (May 2016), 121-129. DOI:https://doi.org/10.5395/rde.2016.41.2.121.

[10] Camino, N. A., Pérez, O. E. and Pilosof, A. M. R. 2009. Molecular and functional modification of hydroxypropylmethylcellulose by high-intensity ultrasound. *Food Hydrocolloids.* 23, 4 (June 2009), 1089-1095. DOI: https://doi.org/10.1016/j.foodhyd.2008.08.015.

[11] Clasen, C. and Kulicke, W.-M. 2001. Determination of viscoelastic and rheo-optical material functions of water-soluble cellulose derivatives. *Progress in Polymer Science.* 26, 9 (November 2001), 1839-1919. DOI:https://doi.org/10.1016/S0079-6700(01)00024-7.

[12] Collins, K. D. 1997. Charge density-dependent strength of hydration and biological structure. *Biophysical Journal.* 72, 1 (January 1997), 65-76.

[13] Desbrieres J, Hirren M, Rinaudo M. 1998. 37, (1998), 145-52.

[14] Fairclough, J. P. A., Yu, H., Kelly, O., Ryan, A. J., Sammler, R. L. and Radler, M. 2012. Interplay between Gelation and Phase Separation in Aqueous Solutions of Methylcellulose and Hydroxypropylmethylcellulose. *Langmuir.* 28, 28 (July 2012), 10551-10557. DOI:https://doi.org/10.1021/la300971r.

[15] Fatimi, A., Tassin, J. F., Quillard, S., Axelos, M. A. V. and Weiss, P. 2008. The rheological properties of silated hydroxypropylmethylcellulose tissue engineering matrices. *Biomaterials.* 29, 5 (February 2008), 533-543. DOI: https://doi.org/10.1016/j.biomaterials.2007.10.032.

[16] Ford, J. L. 1999. Thermal analysis of hydroxypropylmethylcellulose and methylcellulose: powders, gels and matrix tablets. *International Journal of Pharmaceutics.* 179, 2 (March 1999), 209-228. DOI:https://doi.org/10.1016/S0378-5173(98)00339-1.

[17] Fyfe, C. A. and Blazek, A. I. 1997. Investigation of Hydrogel Formation from Hydroxypropylmethylcellulose (HPMC) by NMR Spectroscopy and NMR Imaging Techniques. *Macromolecules.* 30, 20 (October 1997), 6230-6237. DOI:https://doi.org/10.1021/ma970076o.

[18] Gandhi, A., Paul, A., Sen, S. O. and Sen, K. K. 2015. Studies on thermoresponsive polymers: Phase behaviour, drug delivery and biomedical applications. *Asian Journal of Pharmaceutical Sciences.* 10, 2 (April 2015), 99-107. DOI:https://doi.org/10.1016/j.ajps.2014.08.010.

[19] Haque, A. and Morris, E. R. 1993. Thermogelation of methylcellulose. Part I: molecular structures and processes. *Carbohydrate Polymers.* 22, 3 (January 1993), 161-173. DOI:https://doi.org/10.1016/0144-8617(93)90137-S.

[20] Hirren M, Chevillard C, Desbrieres J, Axelos MAV, Rinaudo M. 1998. 39, 25 (1998), 6251-9.

[21] Hofmeister, F. 1888. Zur Lehre von der Wirkung der Salze. *Archiv für experimentelle Pathologie and Pharmakologie.* 24, 4-5 (February 1888), 247-260. DOI:https://doi.org/10.1007/BF01918191.

[22] Hussain, S., Keary, C. and Craig, D. Q. M. 2002. A thermorheological investigation into the gelation and phase separation of hydroxypropyl methylcellulose aqueous systems. *Polymer.* 43, 21 (October 2002), 5623-5628. DOI:https://doi.org/10.1016/S0032-3861(02)00430-5.

[23] Jain, S., Sandhu, P. S., Malvi, R. and Gupta, B. 2013. Cellulose Derivatives as Thermoresponsive Polymer: An Overview. http://www.japsonline.com/counter.php?aid=1149. (December 2013).

[24] Joshi S. C. and Lam Y. C. 2006. Modeling heat and degree of gelation for methyl cellulose hydrogels with NaCl additives. *Journal of Applied Polymer Science.* 101, 3 (May 2006), 1620-1629. DOI:https://doi.org/10.1002/app.23565.

[25] Joshi, S. C. 2011. Sol-Gel Behavior of Hydroxypropyl Methylcellulose (HPMC) in Ionic Media Including Drug Release. *Materials.* 4, 10 (October 2011), 1861-1905. DOI:https://doi.org/10.3390/ma4101861.

[26] Kundu, P. P. and Kundu, M. 2001. Effect of salts and surfactant and their doses on the gelation of extremely dilute solutions of methyl cellulose. *Polymer.* 42, 5 (March 2001), 2015-2020. DOI:https://doi.org/10.1016/S0032-3861(00)00506-1.

[27] Larsson, M., Viridén, A., Stading, M. and Larsson, A. 2010. The influence of HPMC substitution pattern on solid-state properties. *Carbohydrate Polymers.* 82, (July 2010), 1074-1081. DOI:https://doi.org/10.1016/j.carbpol.2010.06.030.

[28] Li, C. L., Martini, L. G., Ford, J. L. and Roberts, M. 2005. The use of hypromellose in oral drug delivery. *Journal of Pharmacy and Pharmacology.* 57, 5 (May 2005), 533-546. DOI:https://doi.org/10.1211/0022357055957.

[29] Li, L. 2002. Thermal Gelation of Methylcellulose in Water: Scaling and Thermoreversibility. *Macromolecules.* 35, 15 (July 2002), 5990-5998. DOI:https://doi.org/10.1021/ma0201781.

[30] Li, L., Shan, H., Yue, C. Y., Lam, Y. C., Tam, K. C. and Hu, X. 2002. Thermally Induced Association and Dissociation of Methylcellulose in Aqueous Solutions. *Langmuir.* 18, 20 (October 2002), 7291-7298. DOI: https://doi.org/10.1021/la020029b.

[31] Liu S. Q., Joshi Sunil C. and Lam Y. C. 2008. Effects of salts in the Hofmeister series and solvent isotopes on the gelation mechanisms for hydroxypropylmethylcellulose hydrogels. *Journal of Applied Polymer Science*. 109, 1 (April 2008), 363-372. DOI:https://doi.org/10.1002/app.28079.

[32] Mitchell, K., Ford, J. L., Armstrong, D. J., Elliott, P. N. C., Rostron, C. and Hogan, J. E. 1990. The influence of additives on the cloud point, disintegration and dissolution of hydroxypropylmethylcellulose gels and matrix tablets. *International Journal of Pharmaceutics*. 66, 1 (December 1990), 233-242. DOI:https://doi.org/10.1016/0378-5173(90)90404-R.

[33] Mombelli, A. and Samaranayake, L. P. 2004. Topical and systemic antibiotics in the management of periodontal diseases. *International Dental Journal*. 54, 1 (February 2004), 3-14.

[34] Nokhodchi, A., Raja, S., Patel, P. and Asare-Addo, K. 2012. The Role of Oral Controlled Release Matrix Tablets in Drug Delivery Systems. *BioImpacts: BI*. 2, 4 (2012), 175-187. DOI:https://doi.org/10.5681/bi.2012.027.

[35] Pearce, E., Larsen, M. and Coote, G. 1999. Fluoride in enamel lining pits and fissures of the occlusal groove-fossa system in human molar teeth. *Caries Research*. 33, 3 (June 1999), 196-205. DOI:https://doi.org/10.1159/000016517.

[36] Pérez, O. E., Wargon, V. and M. R. Pilosof, A. 2006. Gelation and structural characteristics of incompatible whey proteins/hydroxypropylmethylcellulose mixtures. *Food Hydrocolloids*. 20, 7 (October 2006), 966-974. DOI:https://doi.org/10.1016/j.foodhyd.2005.11.005.

[37] Sahoo, C. K., Rao, S. R. M. and Sudhakar, M. 2015. HPMC a biomedical polymer in pharmaceutical dosage forms. *Journal of Chemical and Pharmaceutical Sciences*. 8, (January 2015), 875-881.

[38] Sangfai, T., Tantishaiyakul, V., Hirun, N. and Li, L. 2017. Microphase Separation and Gelation of Methylcellulose in the Presence of Gallic Acid and NaCl as an <Emphasis Type="Italic">In Situ</Emphasis>Gel-Forming Drug Delivery System. *AAPS PharmSciTech*. 18, 3 (April 2017), 605-616. DOI:https://doi.org/10.1208/s12249-016-0546-7.

[39] Seeton, C. J. 2006. Viscosity-Temperature Correlation for Liquids. (January 2006), 131-142. DOI:https://doi.org/10.1115/IJTC2006-12139.

[40] Shoaib, M. H., Al Sabah Siddiqi, S., Yousuf, R. I., Zaheer, K., Hanif, M., Rehana, S. and Jabeen, S. 2010. Development and Evaluation of Hydrophilic Colloid Matrix of Famotidine Tablets. *AAPS PharmSciTech*. 11, 2 (April 2010), 708-718. DOI:https://doi.org/10.1208/s12249-010-9427-7.

[41] Silva, S. M. C., Pinto, F. V., Antunes, F. E., Miguel, M. G., Sousa, J. J. S. and Pais, A. A. C. C. 2008. Aggregation and gelation in hydroxypropylmethyl cellulose aqueous solutions. *Journal of Colloid and Interface Science*. 327, 2 (November 2008), 333-340. DOI:https://doi.org/10.1016/j.jcis.2008.08.056.

[42] Švarc-Gajić, J., Stojanović, Z., Vasiljević, I. and Kecojević, I. 2013. Determination of fluorides in pharmaceutical products for oral hygiene. *Journal of Food and Drug Analysis*. 21, 4 (December 2013), 384-389. DOI:https://doi.org/10.1016/j.jfda.2013.08.006.

[43] The Dow Chemical Company. 2000. [Accessed Oct. 2, 2011].—Google Search: https://www.google.com/search?ei=m37CWs7-Eem4jwT-2paABA&q=The+Dow+Chemical+Company.+2000.+%5BAccessed+Oct.+2.+2011%5 D.+&oq=The+Dow+Chemical+Company.+2000.+%5BAccessed+Oct.+2.+2011%5D.+&gs_l=psy-ab.3..35i39k1.13315.23918.0.24837.125.30.0.0.0.0.247.1713.15j3j1.20.0....0...1c.1.64.psy-ab..108.17.1532.6 . . . 106.OCj08dGw_uQ. Accessed: 2018-04-02.

[44] USP Monographs: Hypromellose: 1980. http://www.pharmacopeia.cn/v29240/usp29nf24s0_m39215.html. Accessed: 2018-04-20.

[45] del Valle, L. J., Díaz, A. and Puiggali, J. 2017. Hydrogels for Biomedical Applications: Cellulose, Chitosan, and Protein/Peptide Derivatives. *Gels*. 3, 3 (July 2017), 27. DOI:https://doi.org/10.3390/gels3030027.

[46] Viridén, A., Wittgren, B., Andersson, T. and Larsson, A. 2009. The effect of chemical heterogeneity of HPMC on polymer release from matrix tablets. *European Journal of Pharmaceutical Sciences*. 36, 4 (March 2009), 392-400. DOI:https://doi.org/10.1016/j.ejps.2008.11.003.

[47] Wu, H., Du, S., Lu, Y., Li, Y. and Wang, D. 2014. The application of biomedical polymer material hydroxy propyl methyl cellulose (HPMC) in pharmaceutical preparations. *Journal of Chemical and Pharmaceutical Research*. 6, (January 2014), 155-160.

[48] Xu, Y., Li, L., Zheng, P., Lam, Y. C. and Hu, X. 2004. Controllable Gelation of Methylcellulose by a Salt Mixture. *Langmuir*. 20, 15 (July 2004), 6134-6138. DOI: https://doi.org/10.1021/1a049907r.

[49] Xu, Y., Wang, C., Tam, K. C. and Li, L. 2004. Salt-Assisted and Salt-Suppressed SolGel Transitions of Methylcellulose in Water. *Langmuir*. 20, 3 (February 2004), 646-652. DOI:https://doi.org/10.1021/la0356295.

[50] Yoo, Y. J. and Um, I. C. 2013. Examination of thermogelation behavior of HPMC and HEMC aqueous solutions using rheology. *Korea-Australia Rheology Journal*. 25, 2 (May 2013), 67-75. DOI:https://doi.org/10.1007/s13367-013-0007-8.

EXAMPLES

Materials and Methods

Hypromellose

In this work, the cellulose derivative used was hydroxypropyl methylcellulose or hypromellose (HPMC) with the trade name of Methocel® E4M, obtained from Colorcon, Inc. (Harleysville, Pa., USA). The percentage of methoxy and hydroxypropoxy substitution were 28-30, 7-12 respectively.

The HPMC was odorless and tasteless, appearing as a white fine powder. This type of HPMC has an average degree of substitution of 1.8 and molecular weight in the range of 300000-500000, as provided by the distributor. The viscosity range for a 2% w/v aqueous solution at 20° C. was 2,663-4,970 mPa·s, as indicated by manufacturer.

Gelling Aid Additives

Sodium fluoride and sodium chloride powder were provided by the Sigma-Aldrich Company (St. Louis, Mo., USA).

HPMC Solution Preparation

To prepare an HPMC solution a hot/cold technique was used. In this method half of the total required volume of water was heated to at least 90° C. to prevent powder agglomeration, then the pre-weighed Methocel E4M powder was added to the water whilst stirring. Stirring continued once the powder was fully dispersed. After that, the remainder of the water was added to the solution as cold water. The solution was then kept in an ice bath until the solution reached the temperature at which the HPMC becomes water-soluble. At this temperature, a transparent solution is observed. It is recommended to keep the solution in the refrigerator overnight for full hydration [5].

HPMC (2% w/v) was prepared according to the technique explained above for this study and it was stored in the refrigerator before use.

HPMC/NaCl and HPMC/NaF Samples Preparation

To prepare samples containing gelling aids, the appropriate amount of NaCl or NaF were dissolved in cold water. The volume of cold water was half of the total required volume of water for the correct final % w/v for the appropriate gelling aid. Then HPMC powder was dispersed in the remaining water volume (hot water). The required gelling aid cold water solution (either NaCl or NaF) was added to the HPMC dispersion. Further cooling allowed the HPMC to dissolve into solution.

For NaCl four different concentrations were prepared: 1, 2, 3, or 4% w/v. For NaF, three different concentrations were prepared: 1, 2, or 3% w/v. As mentioned earlier, each salt has a concentration limit above which gel forming happens below or at room temperature [49].

Analytical Methods to Determine Thermal Gelation of HPMC

Rheological Analysis

Rheology is the most direct and reliable way to determine the sol-gel transition temperature, as well as characterize the rheological properties of both solution and subsequent gel [29]. As a result, a rheometer was chosen to determine the sol-gel transition temperature of the HPMC solutions disclosed. Rheological properties such as dynamic moduli G', G", and complex viscosity $\eta^*$ change when the temperature is in the vicinity of the sol-gel transition. The rheometer is able to measure these properties during heating.

During the routine measurements in these studies, the following procedure was observed: (i) Each HPMC solution was placed on to the bottom Peltier plate of the Discovery Hybrid HR-2 rheometer (TA Instruments, Newcastle, Del., USA) equipped with a Peltier concentric cylinder temperature system and a 50 mm parallel plate; (ii) Oscillation temperature sweep was performed to determine the effect of temperatures on complex viscosity ($\eta^*$), storage modulus (G'), and loss modulus (G") at angular frequency of 1 rad/s and stress applied was 0.4 Pa; (iii) In this study samples were heated in the range of 10-80° C. at a rate of 1° C./min. A thin layer of low-viscosity silicon oil was placed around the sample to prevent dehydration during measurements; (iv) All measurements were repeated in triplicate. The abrupt increase in G', which is accompanied by a sharp increase in viscosity was considered to be a suitable way to define a thermal gelation temperature [30].

Analysis of Fluoride Convention Using a Fluoride-Selective Electrode

The fluoride combination electrode (Thermo Fisher Scientific, Waltham, Mass., USA) was used for fluoride determination. First the standards, having known fluoride concentration, were measured with the fluoride ion selective electrode and ion meter to ensure calibration. Four standards in 10, 50, 500, and 1000 ppm (µg/mL) were used since the maximum amount of fluoride in our sample was theoretically calculated to be approximately 500 ppm. All standards and samples include total ionic strength adjustment buffers (TISABs) which require to adjust the pH and prevent complex formation between $H^+$ and $F^-$ in acidic solutions [42].

Figure 2:
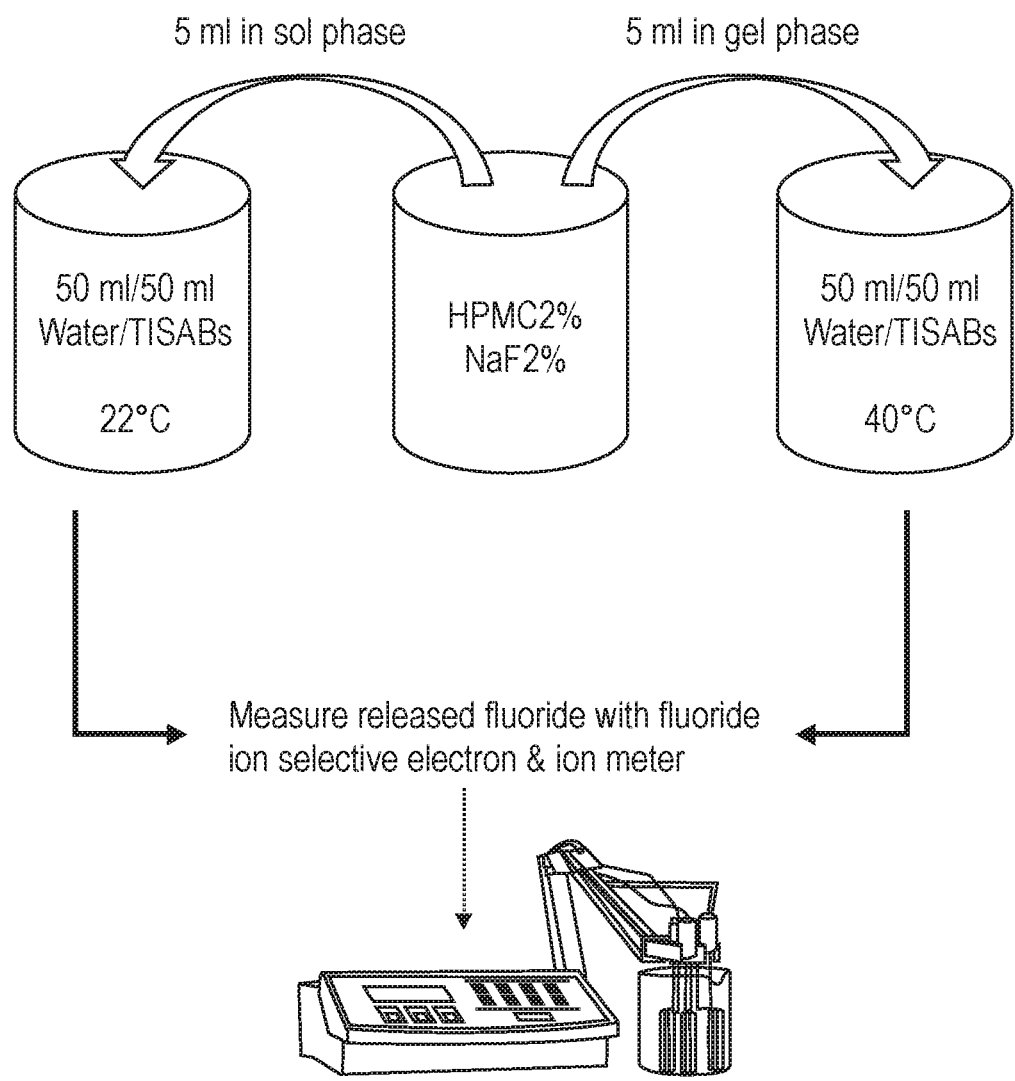
FIG. 2 is a schematic illustration of an experiment comparing the rate of releasing fluoride using a fluoride ion selective electrode and an ion meter.

For the solution measurement, 5 mL of a 2% w/v HPMC with 2% w/v NaF was taken and poured into 50 mL of deionized water and 50 mL TISABs at 22° C. (below the determined gelation temperature, so as to stay in as a solution). Separately, 5 mL of an identical 2% w/v HPMC/NaF was heated to form the gel, and then placed into 50 mL of deionized water with 50 mL of TISABs at 40° C. (above the $T_{Gel}$ so as to maintain the gel). In each case, the fluoride release was determined over a three-minute period using the specific ion electrode. This method is depicted in FIG. 2.

Rheological Analysis

Statistical differences in the thermal gelation temperature of different hypromellose formulations containing different halide salt concentrations were determined using a one-way ANOVA test using Microsoft Excel Analysis Toolpak (Microsoft Inc., Redmond, Wash.). P values of <0.05 were considered statistically significant.

Fluoride Release Rate Comparison

A dissolution profile comparison was used to assess the similarity of the fluoride drug release from either a liquid "sol" state or a pre-gelled state. Using this approach, the similarity factor ($f_2$) was used to compare the two drug release profiles. The similarity factor ($f_2$) is a logarithmic reciprocal square root transformation of the sum of squared error and is a measurement of the similarity in the percent (%) dissolution between the two curves, this is represented by Equation 1, below:

$$f_2 = 50 \times \log\left[\left(1 + (1/n)\sum_{t=1}^{n}(R_t - T_t)^2\right)^{-0.5} \times 100\right] \quad (1)$$

Where n is the number of time points, R represents the fluoride release of the "sol" sample batch at time t, and T is the fluoride release of the gel sample at time t.

Using this approach $f_2$ values greater than 50 mean that there is less than 10% difference between the two release profiles, indicating that they are similar.

Results

Effect of NaCl and NaF on Thermogelation of a 2% w/v HPMC E4M Solution

Figure 3:
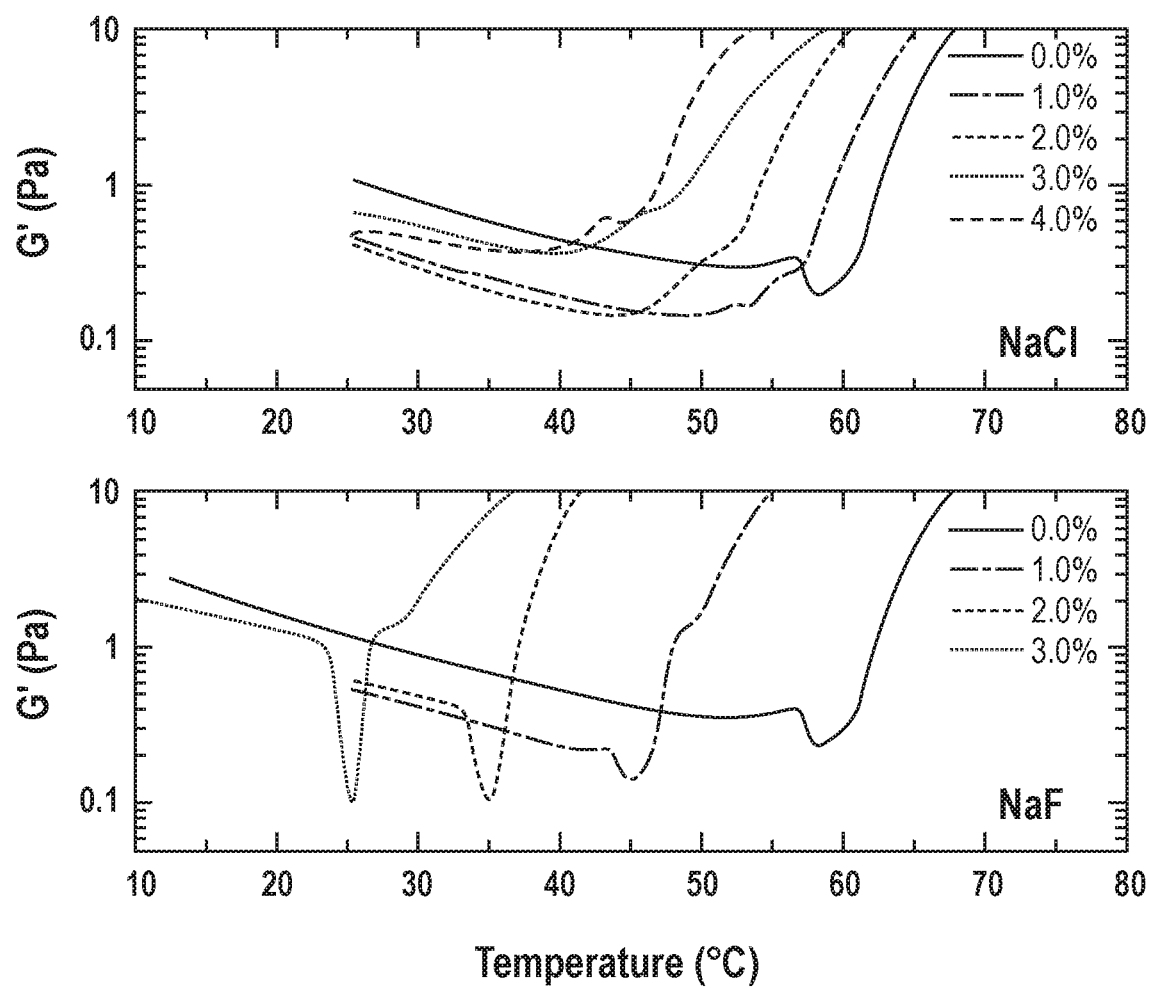
FIG. 3 is a graph showing the storage modulus (G') of 2% w/v E4M (HPMC) and the mixtures of HPMC and various concentrations of NaCl and NaF during heating from 10 to 80° C.
Figure 4:
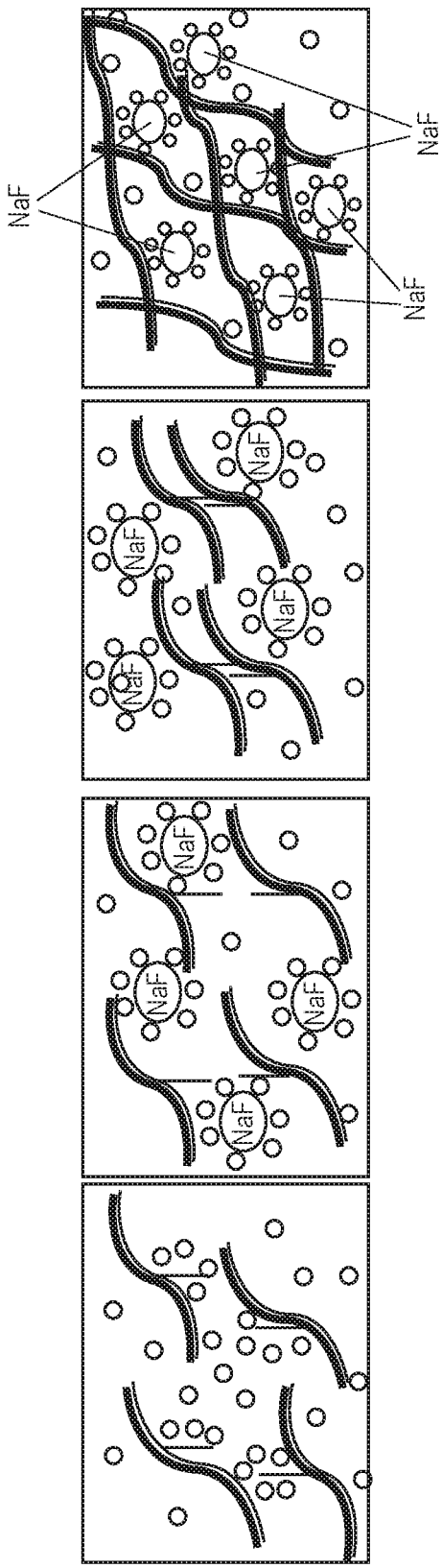
FIGS. 4A-4D provide a schematic illustration of the sol-gel transformation for an aqueous solution of HPMC with NaF.

FIG. 3 shows the temperature dependence of the storage modulus (G') of 2% w/v E4M (HPMC) and the mixtures of 1-4% w/v NaCl or 1-3% NaF w/v during heating from 10 to 80° C. Total volume is 100 ml (v=100). The abrupt increase of G' which is defined as the gelation temperature shifted to the left or to a lower temperature by increasing both NaCl and NaF concentrations.

TABLE 2

Thermal gelation temperature of HPMC/NaCl for three independent experiments.

| | Concentration of NaCl (%) | | | | |
|---|---|---|---|---|---|
| Sample | 0 | 1 | 2 | 3 | 4 |
| 1 | 59.9 | 55.5 | 50.3 | 47 | 44.3 |
| 2 | 60.4 | 53.3 | 49.6 | 47.8 | 44.4 |
| 3 | 60.7 | 54.8 | 50.5 | 46.4 | 43.7 |
| Mean | 60.3 | 54.5 | 50.13 | 47.07 | 44.13 |
| SD | 0.33 | 0.91 | 0.39 | 0.57 | 0.31 |
| % RSD | 0.55 | 1.68 | 0.77 | 1.22 | 0.70 |

TABLE 3

Thermal gelation temperature of HPMC/NaF (n = 3).

| Sample | Concentration of NaF (%) | | | |
|---|---|---|---|---|
| | 0 | 1 | 2 | 3 |
| 1 | 59.9 | 46.2 | 35 | 17.6 |
| 2 | 60.4 | 44.8 | 33.2 | 16.1 |
| 3 | 60.7 | 42.8 | 32 | 16.1 |
| Mean | 60.3 | 44.6 | 33.4 | 16.6 |
| SD | 0.32 | 1.39 | 1.23 | 0.71 |
| % RSD | 0.55 | 3.12 | 3.69 | 4.25 |

The gelation temperature of HPMC, 1% NaCl/HPMC, 2% NaCl/HPMC, 3% NaCl/HPMC, and 4% NaCl/HPMC are 61.6, 57.1, 52.6, 47.2, and 44.2° C., respectively. Using a one-way ANOVA, it was observed that that each value obtained for G' were all statistically significantly different from each other for HPMC 2910 samples containing NaCl (P<0.05).

The abrupt increase in G' also shifts to the lower temperature with an increasing NaF concentration. The sol-gel temperatures of 1% NaF/HPMC, 2% NaF/HPMC, and 3% NaF/HPMC are 49.6, 40.4, and 28.9° C., respectively. Using a one-way ANOVA, it was observed that that each value obtained for G' were all statistically significantly different from each other for HPMC 2910 samples containing NaF (P<0.05).

The results show that both NaCl and NaF belong to the "salt-out" category, attracting water molecules to surround them which leads to the disruption of water cages around the hydrophobic methoxy groups of HPMC. As a result, the methoxy groups are exposed at lower temperatures, which in turn results in a lower thermal gelation temperature ($T_{Gel}$). The results further demonstrate that an equivalent amount of NaF reduces the $T_{Gel}$ of HPMC 2910 more than NaCl. The larger effect on $T_{Gel}$ with NaF supports our hypothesis that the fluoride anion ($F^-$) being more electronegative than the chloride anion ($Cl^-$), attracts water molecules to a greater extent resulting in a higher degree of hydrophobic aggregation and ultimately gelation at lower temperature. These results show that the effect of these two salts on thermogelation of HPMC 2910 correlates well with the order of the Hofmeister series ($F^->Cl^-$).

FIG. 4A-4D provide a schematic representation of how NaF can affect the sol-gel transition temperature of HPMC compared to a salt-free HPMC solution. As described earlier the addition of a gelling aid such as sodium fluoride has a comparable effect to that of increasing the temperature, essentially resulting in the disruption of water "cages" that surround the hydrophobic methoxy groups (Compare FIGS. 4A and 4B). This effect occurs as the ability of sodium fluoride to interact with water molecules is greater than that of the HPMC polymer. Hence, the methoxy groups are exposed at lower temperatures, enabling the hydrophobic association to occur. (FIG. 4C) In short, hydrogels of HPMC that include NaF as a gelling aid (FIG. 4D) are formed at lower temperatures than pure HPMC.

Here, we consider a linear dependence between gelation temperature and concentration of selected additives [49]. Therefore, the following relationship between gelation temperature ($T_{Gel}$) and additive composition (x) can be applied:

$$T_{Gel}=T_0-\alpha_G x \qquad (2)$$

Where, $T_0$ is the gelation temperature of pure HPMC and $\alpha_G$ is the rate of change in gelation temperature as a function of additive composition. The parameter $T_0$ is strongly dependent on HPMC concentration and type of HPMC, which is related to the nature and the quantity of the substituent groups attached to the anhydroglucose glucose ring [43]. If one considers a 2% w/v HPMC 2910 solution, $\alpha_G$ should be strongly dependent on the additives and their electronegativity.

Figure 5:
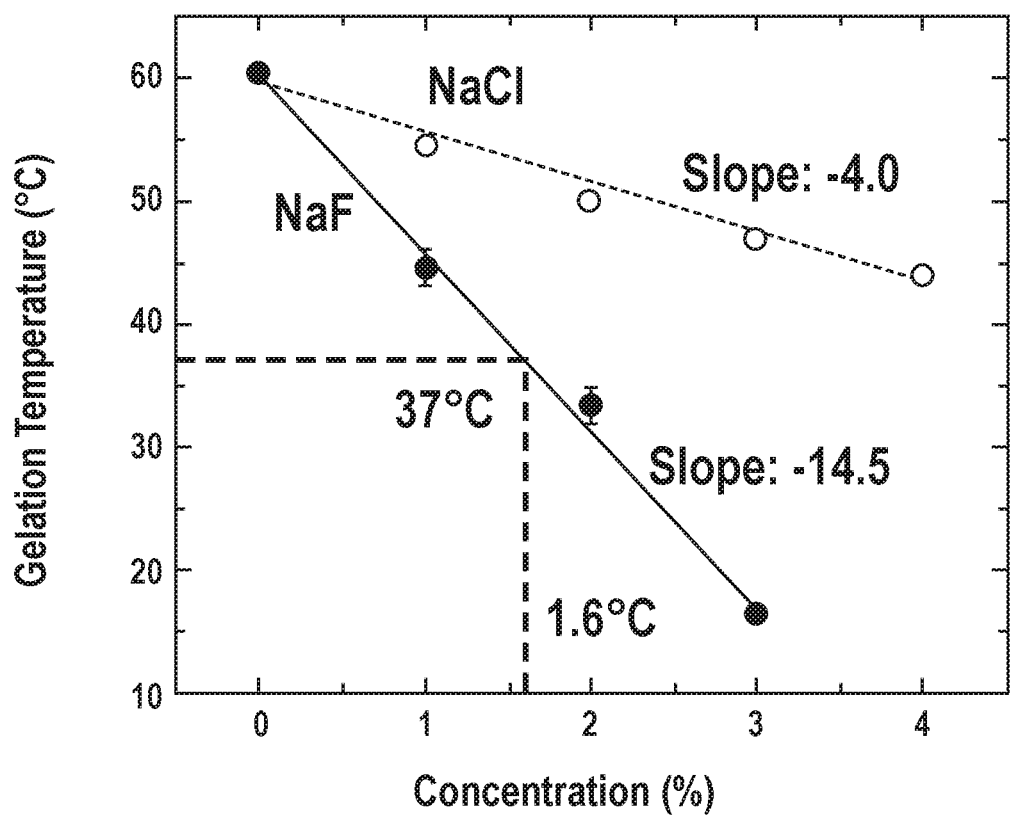
FIG. 5 is a graph showing the gelation temperature of 2% w/v E4M (HPMC) and the mixtures of HPMC and various concentrations of NaCl and NaF as a function of temperature.

FIG. 5 exhibits a comparison between the NaF and NaCl in terms of reducing the gelation temperature of 2% w/v HPMC 2910. The thermal gelation temperature for each data point is an average of the rheological measurement, the error bar represents the standard deviation (n=3). As expected, a decrease was observed upon increasing the concentration of both NaCl and NaF. The results were fitted using the function described in Equation 1, with an R-square value above 0.98, indicating good linearity of the data set. The gelation temperature of a pure 2% w/v HPMC solution ($T_0$) was found to be ~60° C., and is considered to be independent of the nature of the additive used in the experiment. This value was found to be close to the reported values in literature for HPMC 2910 with similar concentrations [5]. A high value of $\alpha_G$ was obtained for NaF ($\alpha_{G-NaF}$~14.5) which is greater by a factor of ~3.6 times that of the corresponding value obtained for NaCl ($\alpha_{G-NaCl}$~4.0). This can be attributed to the high electronegativity of $F^-$ relative to $Cl^-$.

Figure 6:
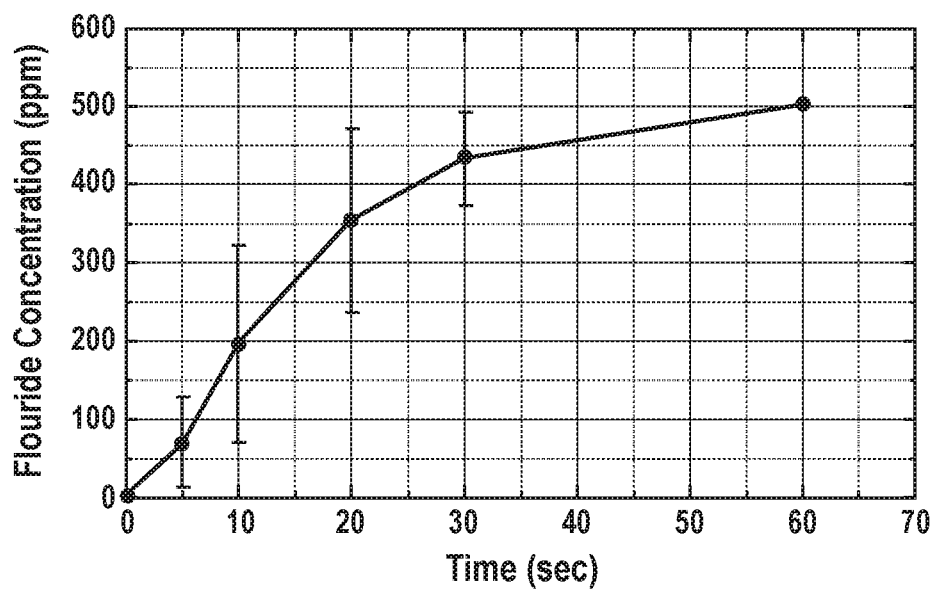
FIG. 6 is a graph showing the concentration of fluoride release as a function of time for solution.
Figure 7:
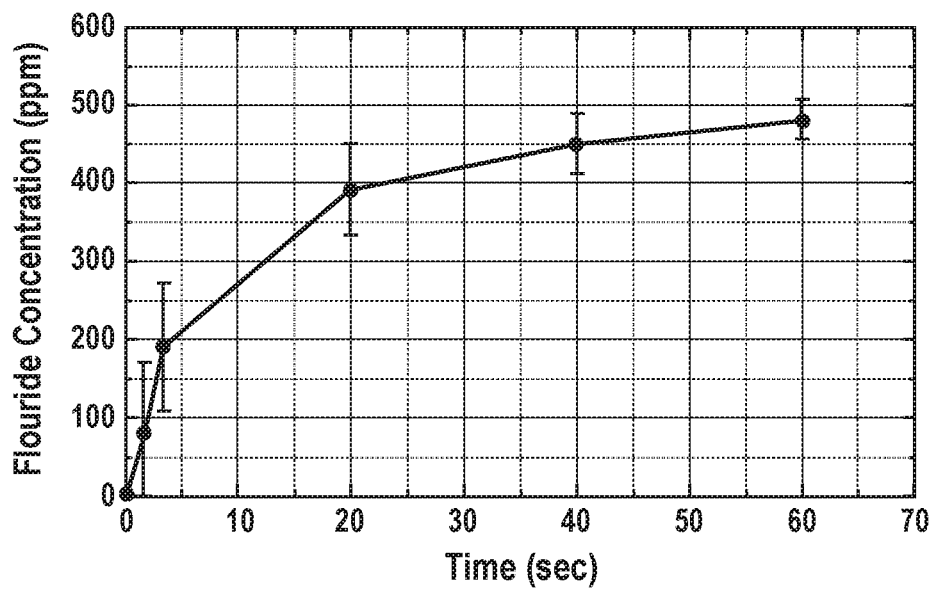
FIG. 7 is a graph showing the concentration of fluoride release as a function of time for gel.

NaF has the potential to prevent and/or reverse tooth decay. Therefore, a mixture of HPMC and NaF could be used as a potential application for in situ gelation that would prolong release of fluoride to a specific site. By reducing the gelation temperature of HPMC to body temperature, it is feasible to apply the fluoride in a low viscosity solution and apply it into a deep pit or fissure of a tooth (which is currently inaccessible with higher viscosity applications). The affected tooth area might then receive fluoride over a sustained period after the HPMC in solution subsequently gels rapidly at body temperature. It is known that the higher the contact time for fluoride on an effected tooth, the greater the extent of remineralization [9] FIG. 6 shows that the maximum amount of fluoride is released in 40 seconds, as a solution or "sol" phase. Conversely, FIG. 7 shows that it took 120 seconds for the complete fluoride release from the gel (with an identical formulation but above the $T_{Gel}$). Thus, the release rate of fluoride from the gel was found to be three times slower than that of the solution. Since this is the highest molecular weight available for Hypromellose 2910, then there is an extensive methoxy hydrophobic interaction for each high molecular weight HPMC polymer chain; leading to a slower rehydration and slow reversal of the sol-gel transition. In fact, it was observed that the gel remained for approximately 1 hour following complete diffusion of the NaF from the 3D gel matrix. It is conceivable that a smaller molecular weight HPMC grade might disperse more quickly. Additionally, using the higher molecular weight HPMC 2910 grade, it was observed that the gel still remained following complete release of fluoride into the bulk solution. In this case it is likely that there is a period that rehydration of the methoxy groups must occur before dissolution and dispersion of the gel can proceed. Again, it is likely that this dispersion of the gel following complete fluoride release would be quicker with a lower molecular weight HPMC grade.

Figure 8:
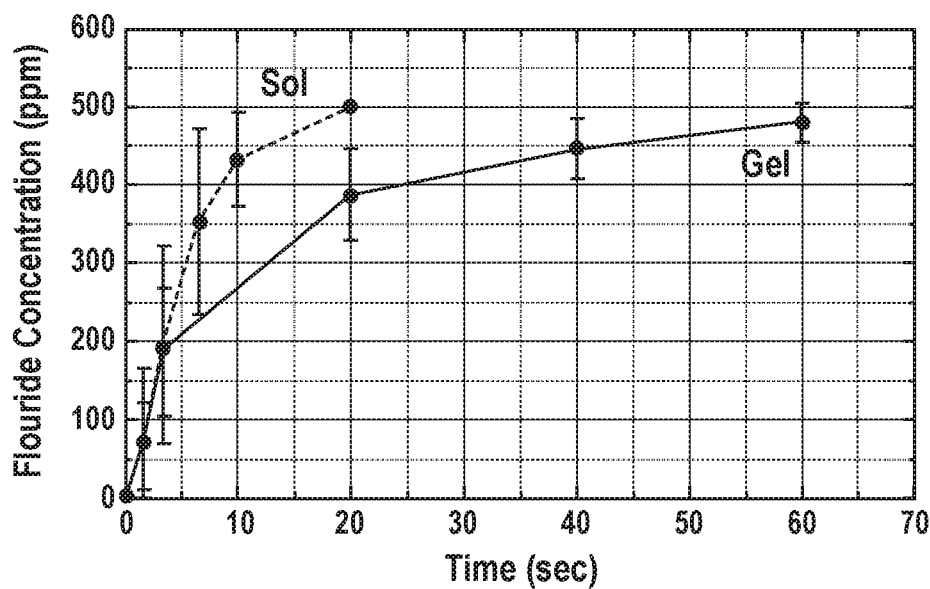
FIG. 8 is a graph showing the concentration of fluoride release as a function of time for both solution and gel.

FIG. 8 compares the rate of fluoride release from solution and gel. It is apparent that the total amount of NaF released from the gel takes a longer time compared to that of the solution formulation. However, it should be noted that a fraction of NaF is likely to be on the surface or at the periphery of the hydrogel after it is formed. This fraction is estimated to be approximately 200 ppm, since the release rate of the gel matches that of the liquid for the first 200 ppm fluoride anions detected, before deviation from this immediate release rate by the gelled formulation is seen. A similarly factor evaluation to compare these two release profiles, gave an $f_2$ factor of 5. This value indicates that release profiles for the same HPMC/NaF compositions were not statistically similar.

The examples disclosed herein investigate the effect of NaCl and NaF in the thermal gelation temperature of HPMC 2910 using rheological analysis. It was found that the gelation temperature of HPMC 2910 reduces linearly with increasing additive concentration, when either NaCl or NaF are added as gelling aids. Although the mechanism of the gelation is the same for each gelling aid, a significant difference was observed in the rate of $T_{Gel}$ reduction. NaF was shown to shift the $T_{Gel}$ to a lower temperature significantly more than NaCl. This more significant shift can be attributed to the greater degree of interaction between the fluoride anion and water molecules, compared to the same interaction with water molecules and the chloride anion. Therefore, NaF as a gelling aid, is more effective in reducing the thermal gelation temperature than NaCl.

The experimental results, comparing the rate of fluoride release from a solution state to that of a gel, indicated that fluoride releases slower when it is entrapped in the gel state. In a hydrogel comprising HPMC and NaF, a fraction of NaF can be considered to be on the on the surface and at the periphery of the hydrogel network, while the bulk of the fluoride in the mixture resides inside that hydrogel network. It was determined that this portion of the fluoride, on the outside and periphery, released at the same rate of a non-gelled solution of the same composition. Furthermore, the amount of fluoride that is considered to be inside the hydrogel matrix releases at a different rate, and over an extended period. Thus, we can conclude that due to the transition of the solution (sol phase) containing fluoride, into the gel phase, release rate of fluoride can be prolonged. This type of fluoride delivery would enable the tooth surface more time to absorb fluoride, and thus likely making it a more effective therapy.

What is claimed is:

1. A gelling liquid formulation comprising a thermoresponsive hydrogel modified with an agent that alters the native gelation point of the thermoresponsive hydrogel to a temperature suitable for gelation in the oral cavity.

2. The gelling liquid formulation of claim 1 wherein the agent is also an active pharmaceutical ingredient.

3. The gelling liquid formulation of claim 1 wherein the modified thermoresponsive hydrogel is a liquid or sol state at ambient temperature and a viscoelastic solid (gel) state at body temperature.

4. The gelling liquid formulation of claim 3 wherein the active pharmaceutical ingredient is selected from the group consisting of: antibiotics, antivirals, antifungals, corticosteroids, non-narcotic analgesics, narcotic analgesics, nonsteroidal anti-inflammatory drugs, and local anesthetics.

5. The gelling liquid formulation of claim 1 further modified with an active pharmaceutical ingredient.

6. A gelling liquid formulation comprising a thermoresponsive hydrogel modified with an agent that alters the native gelation point of the thermoresponsive hydrogel and wherein the gelling liquid has a low enough viscosity to be applied uniformly over the target surface.

7. The gelling liquid formulation of claim 6 wherein the thermoresponsive hydrogel's natural gelation point is at a temperature other than body temperature and the agent modifies the thermoresponsive hydrogel so as to have a gelation point at or below body temperature.

8. A gelling liquid formulation comprising a cellulose derivative thermoresponsive hydrogel modified with an agent that alters the native gelation point of the thermoresponsive hydrogel.

9. The gelling liquid formulation of claim 8 wherein the cellulose derivative is Hypromellose.

10. A gelling liquid formulation comprising a thermoresponsive hydrogel modified with a gelling aid.

11. The gelling liquid formulation of claim 10 wherein the gelling aid is a salt-out ion.

12. The gelling liquid formulation of claim 11 wherein the salt-out ion is derived from NaF.

* * * * *